United States Patent [19]

Duffett

[11] Patent Number: Plant 5,414

[45] Date of Patent: Mar. 12, 1985

[54] CHRYSANTHEMUM PLANT NAMED FOXY

[75] Inventor: William E. Duffett, Salinas, Calif.

[73] Assignee: Yoder Brothers, Inc., Barberton, Ohio

[21] Appl. No.: 505,086

[22] Filed: Jun. 16, 1983

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Foxy having flat capitulum form; daisy capitulum type; red ray floret color; diameter across face of capitulum ranging from 85 to 100 mm. at maturity; uniform late nine week photoperiodic flowering response to short days; tall plant height when grown single stem; 12 to 18 cm. peduncles on open, normally terminal sprays; very slow development of yellow green discs; and 13° C. minimum temperature tolerance for initiation and development of flowering buds with no less than 14 continuous dark hours.

3 Drawing Figures

The present invention comprises a new and distinct cultivar of *Chrysanthemum morifolium,* Ramat., named Foxy.

Foxy is a product of a planned breeding program which had the objective of creating new chrysanthemum cultivars having low temperature tolerance for cut spray mum programs with daisy capitulum type, deep bronze or red ray floret color, nine week flowering response, and the ability to produce commercially acceptable quality in year round programs. Such traits in combination were not present or needed improvement in previously available commercial cultivars.

Foxy was originated from a cross made in a controlled breeding program in Salinas, Calif. in 1978. The female parent was identified as 7717960, an unnamed bronze red daisy seedling originated from a hybridization of two unnamed seedlings. The male parent of Foxy was identified as 773361, an unnamed bronze daisy seedling originated from a cross between Tantalizer, disclosed in U.S. Plant Pat. No. 3,906, and an unnamed seedling.

Foxy was discovered and selected as one flowering plant within the progeny of the stated cross by William E. Duffett on Jan. 15, 1980 in a controlled environment in Salinas, Calif.

The first act of asexual reproduction of Foxy was accomplished when vegetative cuttings were taken from the initial selection in March 1980 in a controlled environment in Salinas, Calif. by a technician working under formulations established and supervised by William E. Duffett.

Horticultural examination of selected units initiated June 20, 1980 has demonstrated that the combination of characteristics as herein disclosed for Foxy are firmly fixed and are retained through successive generations of asexual reproduction.

Foxy has not been observed under all possible environmental conditions. The phenotype may vary significantly with variations in environment such as temperature, light intensity, and day length. The following observations, measurements and comparisons describe plants grown in Salinas, Calif. and Leamington, Canada under greenhouse conditions which approximate those generally used in commercial practice.

The following traits have been repeatedly observed and are determined to be basic characteristics of Foxy which in combination distinguish this chrysanthemum as a new and distinct cultivar:

(1) Flat capitulum form;

(2) Daisy capitulum type;

(3) Red ray floret color;

(4) Diameter across face of capitulum ranging from 85 to 100 mm. at maturity;

(5) Uniform late nine week photoperiodic flowering response to short days;

(6) Long peduncle length, ranging from 12 to 18 mm.;

(7) Very slow development of yellow-green discs;

(8) Tall plant height, requiring 1–2 long day weeks prior to short days to attain a flowered plant height of 80 to 100 cm. for May through October flowerings; and (9) Low temperature tolerance of 13° C. for initiation and development when grown in single stem cut spray programs with a continuous dark period of 14 hours.

The accompanying photographic drawings show typical inflorescence and foliage characteristics of Foxy, with the colors being as nearly true as possible with illustrations of this type. Sheet 1 is a color photograph of Foxy grown as a single stem cut spray. Sheet 2 is a black and white photograph of three views of the inflorescence of Foxy. Sheet 3 is a black and white photograph showing the leaves of Foxy at three stages of development (mature, intermediate and immature).

Of the many commercial cultivars known to the present inventor, the most similar in comparison to Foxy are Firepower, disclosed in U.S. Plant Pat. No. 3,947, and Tuneup, disclosed in U.S. Plant Pat. No. 3,604. Reference is made to attached Chart A which compares certain characteristics of Foxy to those same characteristics of Firepower and Tuneup.

The color of Foxy is a deeper red with less blue than Firepower and is less bronze than Tuneup. All three cultivars are of similar capitulum type and form. Tuneup has the shortest peduncles, the smallest capitulum diameter, and the shortest plant height. Both Firepower and Tuneup are intolerant of 13° C. for bud initiation. Foxy will initiate and develop at 13° C. with a continuous 14 hour dark period.

In the following description, color references are made to The Royal Horticultural Society Colour Chart. The color values were determined between 8:30 A.M. and 9:00 A.M. on Oct. 20, 1982 under 150 foot-candle light intensity at Salinas, Calif.

CLASSIFICATION

Botanical: *Chrysanthemum morifolium,* Ramat., cv FOXY.

Commercial: Spray daisy cut mum.

INFLORESCENCE

Capitulum:

*Form.*—Flat.

*Type.*—Daisy.

*Diameter across face.*—85 To 100 mm.

Corolla of ray florets:

*Color (general tonality from a distance of three meters).*—Red.

*Color (abaxial).*—46A-45A.

*Color (adaxial).*—42B-47A.

Corolla of disc florets:

*Color (mature).*—154A.

*Color (immature).*—145A.

Reproductive organs:

*Androecium.*—Present disc florets only; pollen scant to none.

*Gynoecium.*—Present both ray and disc florets.

PLANT

General appearance:

*Height.*—Tall; 80 to 100 cm., as a flowering plant from a rooted cuttings, with 7-14 long days for May through October flowerings and maintaining a minimum nightly 14 hour continuous dark period.

Foliage:

*Color (abaxial).*—147A.

*Color (adaxial).*—147B.

*Shape.*—Moderately lobed and slightly serrated.

CHART A

COMPARISON OF FOXY, FIREPOWER AND TUNEUP

| CULTIVAR | RAY FLORET COLOR | CAPITULUM FORM AND TYPE | SPRAY FORMATION |
|---|---|---|---|
| FOXY | RED | FLAT DAISY | 12 to 18 cm. PEDUNCLES |
| FIREPOWER | DARK RED | FLAT DAISY | 12 to 18 cm. PEDUNCLES |
| TUNEUP | RED BRONZE | FLAT DAISY | 6 to 12 cm. PEDUNCLES |

| CULTIVAR | DIAMETER ACROSS FACE OF CAPITULUM | PLANT HEIGHT | FLOWERING RESPONSE PERIOD |
|---|---|---|---|
| FOXY | 85 to 100 mm. | TALL 80 to 100 cm. | 9 WEEKS GOOD 13° C. TOLERANCE |
| FIREPOWER | 75 to 100 mm. | TALL 85 to 110 cm. | 10 WEEKS POOR 13° C. TOLERANCE |
| TUNEUP | 60 to 90 mm. | MEDIUM 70 to 90 cm. | 10 WEEKS POOR 13° C. TOLERANCE |

COMPARISONS MADE OF PLANTS GROWN AS SINGLE STEM SPRAY CUT MUMS WITH 7 LONG DAYS IN SALINAS, CALIFORNIA AND LEAMINGTON, CANADA.

I claim:

1. A new and distinct plant of *Chrysanthemum morifolium,* Ramat., named Foxy, as described and illustrated, and particularly characterized as to uniqueness by the combined characteristics of flat capitulum form; daisy capitulum type; red ray floret color; diameter across face of capitulum ranging from 85 to 100 mm. at maturity; uniform late nine week flowering response; tall plant height when grown single stem; 12 to 18 cm. peduncles on open, normally terminal sprays; very slow development of yellow green discs; and 13° C. minimum temperature tolerance for initiation and development of flowering buds with no less than 14 continuous dark hours.

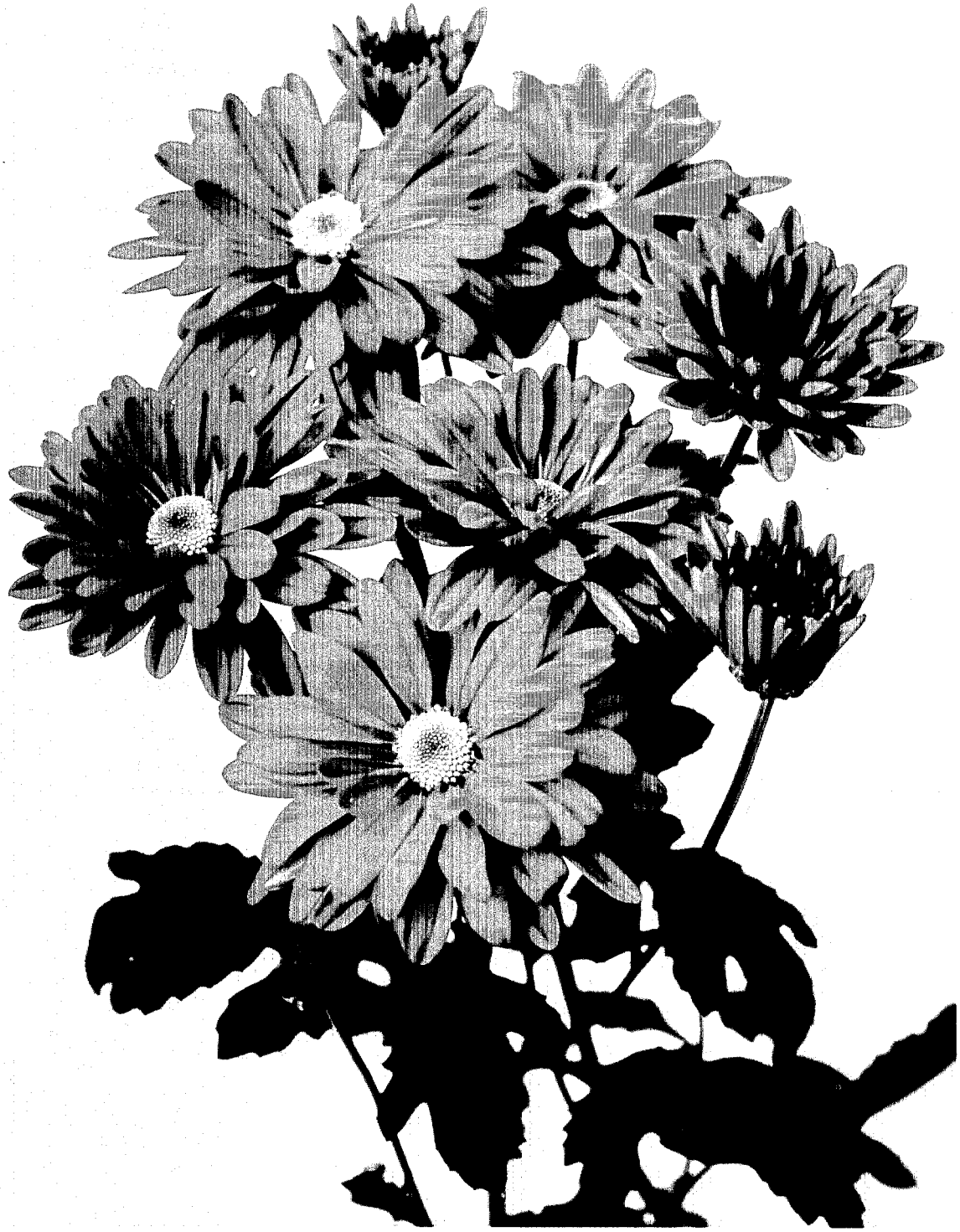

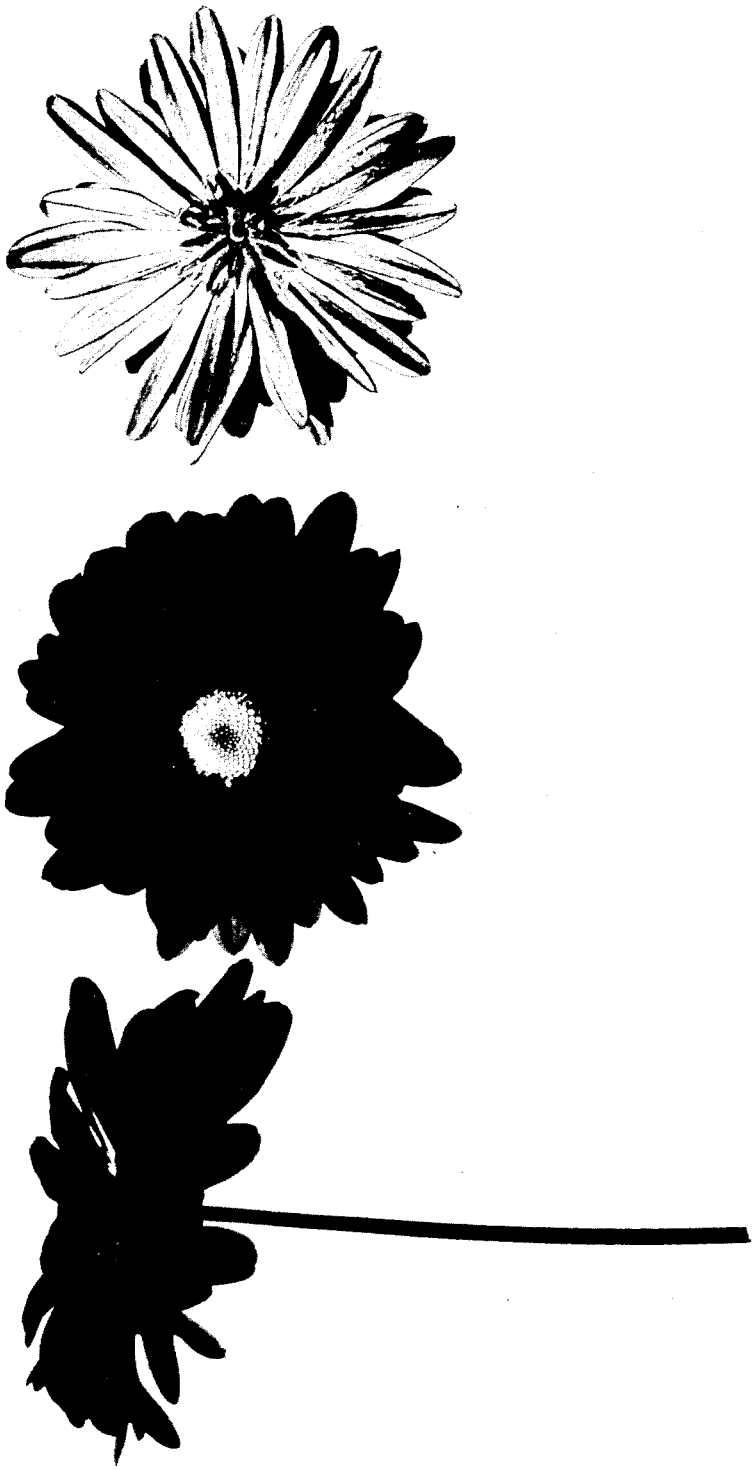

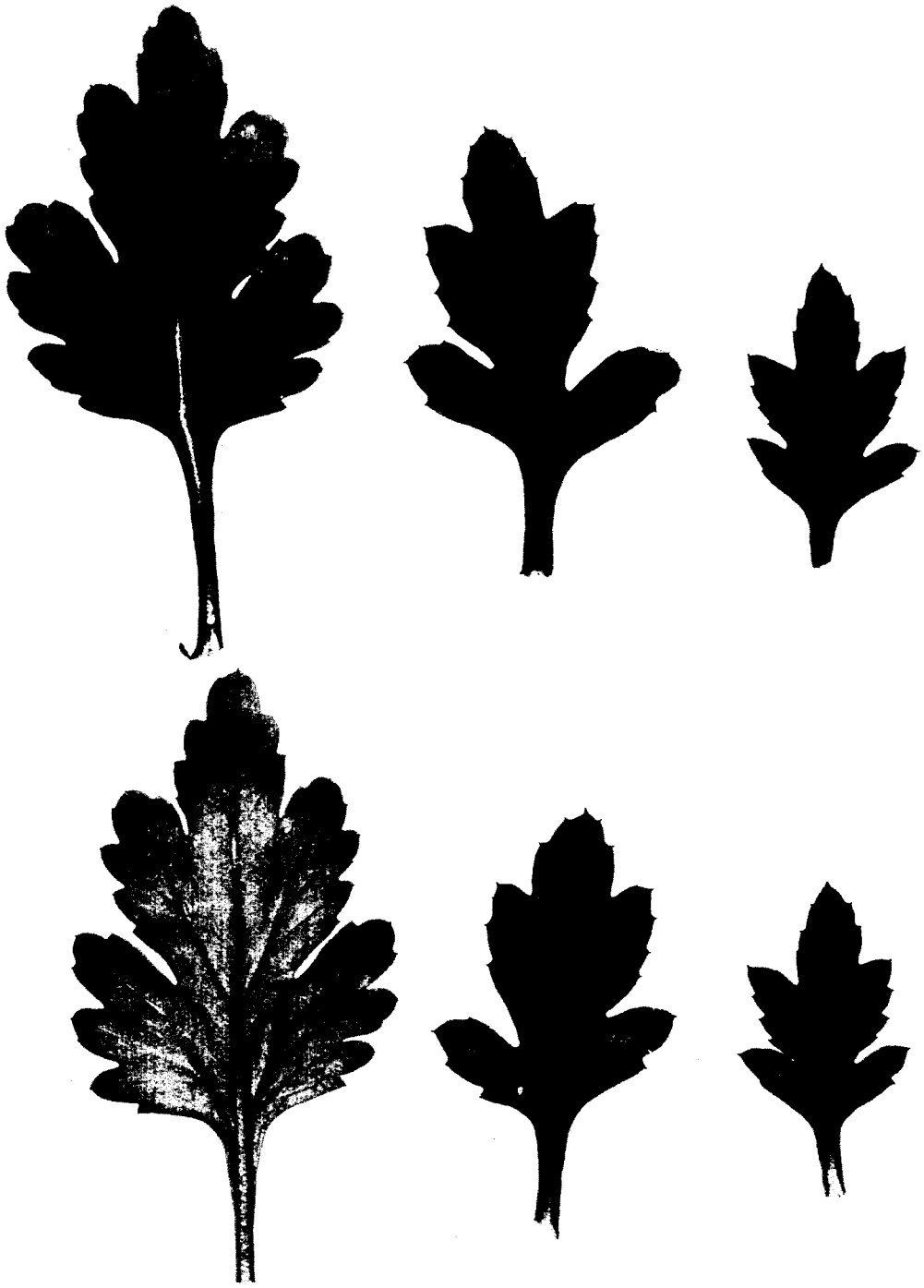

* * * * *